United States Patent [19]

Bartman

[11] Patent Number: 5,026,353
[45] Date of Patent: Jun. 25, 1991

[54] MULTI-CHAMBER SAFETY SYRINGE

[76] Inventor: Thomas F. Bartman, 6601 Langdon Ave., Van Nuys, Calif. 91406

[21] Appl. No.: 565,145

[22] Filed: Aug. 10, 1990

Related U.S. Application Data

[63] Continuation-in-part of Ser. No. 542,886, Jun. 25, 1990, abandoned.

[51] Int. Cl.$^5$ ............................................... A61M 5/32
[52] U.S. Cl. .................................... 604/192; 604/198; 604/263
[58] Field of Search ............... 604/192, 195, 198, 263, 604/187, 110, 228, 220

[56] References Cited

U.S. PATENT DOCUMENTS

| | | | |
|---|---|---|---|
| 2,722,215 | 11/1955 | Dahlgren | 604/228 X |
| 4,838,869 | 6/1989 | Allard | 604/195 |
| 4,874,382 | 10/1989 | Lindemann et al. | 604/195 |

Primary Examiner—John D. Yasko
Attorney, Agent, or Firm—Michael A. Painter

[57] ABSTRACT

A hypodermic syringe incorporating a post-injection safety sheath for enclosing the needle tip. The hypodermic syringe incorporates a central chamber and two slide chambers disposed on opposite sides of, and in parallel spaced relation to the central chamber. The central chamber is used to store fluid being injected into or withdrawn from the patient. The slide chambers enclose compressive apparatus for positioning the protective sheath. A helical compression spring is coaxially aligned within each of the slide chambers, each being coupled to the protective sheath. When the helical springs are positioned in the compressed state, the protective sheath is urged away from the distal end of the needle and maintained in position through a pair of release tabs extending through the walls of the slide chambers. When extended, the needle tip is closed within the protective sheath.

15 Claims, 2 Drawing Sheets

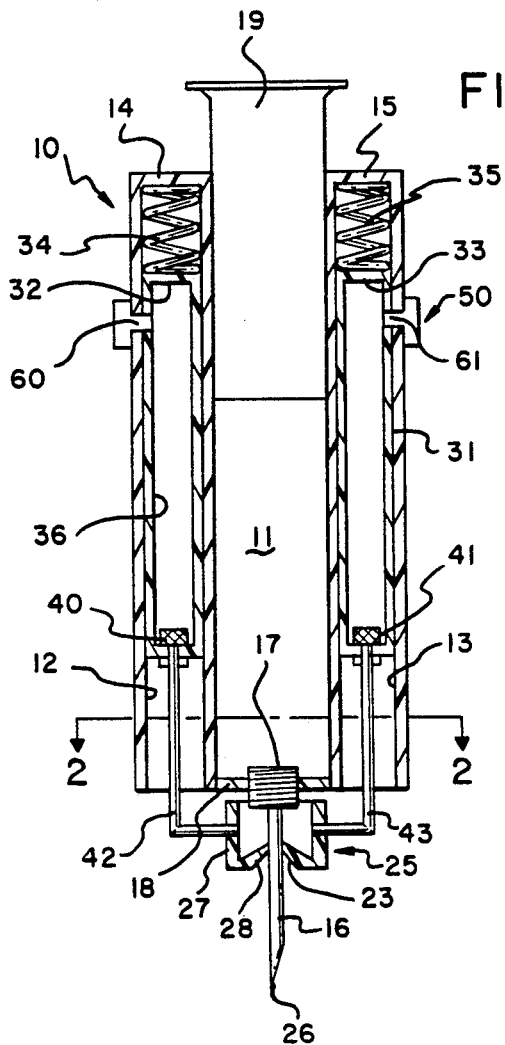
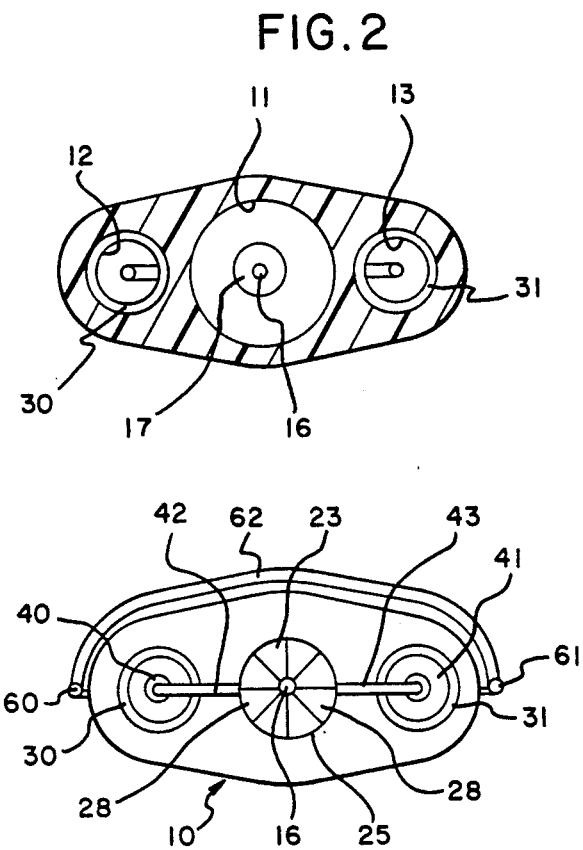
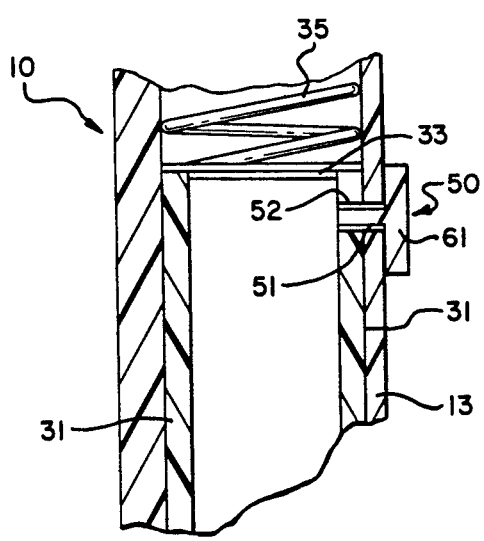
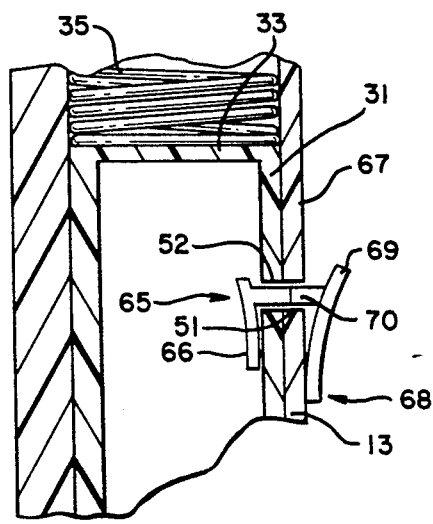
FIG. 1
FIG. 2
FIG. 3
FIG. 4
FIG. 6

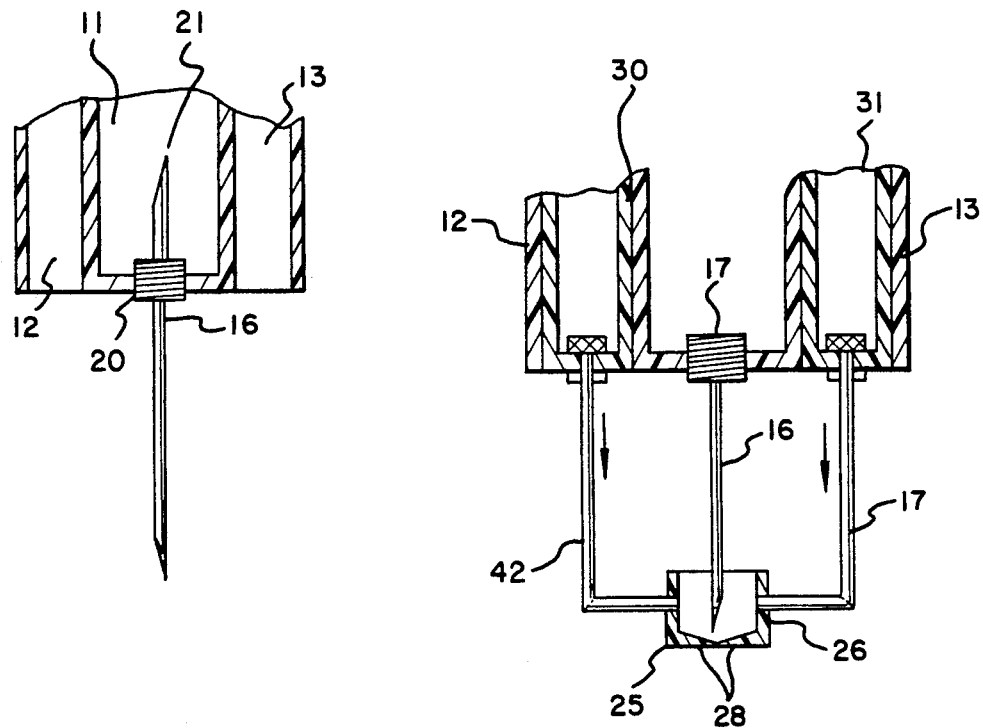
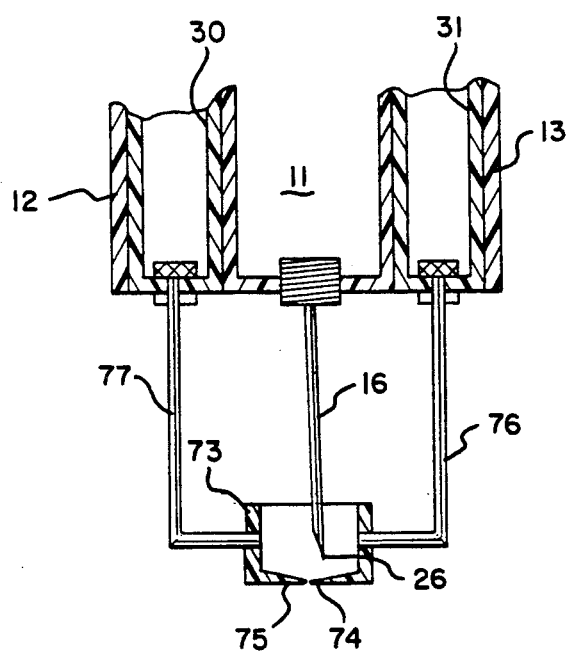

MULTI-CHAMBER SAFETY SYRINGE

BACKGROUND OF THE INVENTION

1. Field of the Invention

The present invention generally relates to devices used for the hypodermic injection of medication into or the withdrawal of fluid from a human patient and, more particularly, with a hypodermic syringe which employs a post-injection protective sheath about the needle tip.

2. Prior Art

The prior art discloses many devices for injecting medication into or withdrawing body fluids from human patients. Typically, devices taught by the prior art include syringes which receive measured quantities of medication to be injected or which can be used to draw samples of the patient's blood. Because these devices utilize injection needles, they are generally of a disposable nature and therefore discarded after a single use. Because of the risk of contamination, it is critical that individuals be protected from inadvertent contact with the needle tip after the hypodermic syringe has been used. This is particularly important when the needles have been applied to patients capable of contaminating the needles with blood-transmitted diseases such as hepatitis or acquired immune deficiency syndrome.

U.S. Pat. No. 4,804,371 is representative of the prior art illustrating post-injection needle sheaths. The fluid chamber and the needle are in axial alignment. The device provides an assembly which employs a compression spring between the body of the needle and a protective cap. Prior to the injection, the distal end of the needle is disposed through an opening in the cap, the cap being in frictional engagement with the body holding the spring in a compressed position. After the injection, the cap is released thereby allowing the spring to extend. When the spring is in the extended condition, the distal end of the needle is misaligned with the opening in the cap so that the distal end is prevented from again passing through the opening in the cap.

The problems inherent in this device are representative of those which are exhibited in other devices which have sought to employ post-injection safety sheaths. The devices taught by the prior art contemplate that the spring will be in a compressed condition during use of the needle and until withdrawn from the patient. In substantially all devices disclosed by the prior art, the protective cap must be dislodged manually. Since the caps are generally maintained in place through a frictional fit, the user must employ both hands, one to hold the syringe, the other to release the protective cap. Since the protective sheaths are substantially adjacent the needle tips, the risk of accidental contact with the distal end of the needle is acute.

The present invention substantially resolves the problems inherent in the devices taught by the prior art. A hypodermic syringe constructed in accordance with the present invention employs three parallel chambers, a central chamber and two adjacent slide chambers located adjacent to and on diametrically opposed sides of the central chamber. The hypodermic needle extends from and is coaxially aligned with the central chamber and is coupled to the central chamber by means of a conventional needle hub. This permits the present invention to be employed both for injecting medication into a patient and, with conventional modifications, for withdrawing blood from the patient. A protective sheath is coupled to two needle sheath guides, each being slidably disposed within one of the slide chambers. A helical spring is disposed intermediate each of the needle sheath guides and the axial terminus of the respective slide chamber. When the springs are extended, the attached protective sheath will enclose the distal end of the needle. When the helical springs are compressed, the needle tip will be exposed for its intended use. A release tab extends laterally into each of the needle sheath guides and the wall of the respective slide chamber wall at a location substantially removed from the distal end of the needle. Either during or after withdrawal of the needle, the exertion of manual force on the release tabs will cause the springs in each of the slide chambers to expand thereby forcing the protective sheath about the distal end of the needle.

SUMMARY OF THE INVENTION

The present invention is a hypodermic syringe which incorporates a protective needle sheath. The syringe comprises a central chamber which is used to store fluid either being injected into or withdrawn from the patient and a pair of slide chambers which are diametrically disposed on either side of the central chamber and are in parallel, equal spaced relation therewith. The needle assembly is of conventional construction, extending from the central chamber and being coaxial therewith. The needle assembly employs a conventional needle hub which allows the needle to communicate directly with the central chamber. A needle sheath guide is disposed within each of the slide chambers, a helical compression spring being disposed intermediate the axial terminus of the slide chamber and the sheath guide. A protective needle sheath is slidably disposed about the needle and is coupled intermediate the sheath guides. The sheath guides, when urged toward the terminus of the slide chambers opposite the needle compress the helical springs. The helical springs are maintained in a compressed state by release tabs which, when removed, allow the helical springs to expand thereby forcing the attached protective needle sheath to enclose the distal end of the needle.

It is therefore an object of the present invention to provide an improved hypodermic syringe incorporating a protective sheath.

It is another object of the present invention to provide a hypodermic syringe incorporating a protective sheath which can be used for both injecting medication and for withdrawing blood from the patient employing conventional vacuum evacuation tubes.

It is still another object of the present invention to provide a hypodermic syringe which incorporates a protective sheath which can be activated prior to the withdrawal to the needle from the patient.

It is still yet another object of the present invention to provide a hypodermic needle incorporating a protective sheath which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

BRIEF DESCRIPTION OF THE DRAWING

FIG. 1 is a side elevation, partial cross-sectional view of a hypodermic syringe in accordance with the present invention.

FIG. 2 is a cross-sectional view of the hypodermic syringe shown in FIG. 1 taken through line 2—2 of FIG. 1.

FIG. 3 is a bottom plan view of the present invention hypodermic syringe shown in FIG. 1.

FIG. 4 is an enlarged, fragmentary cross-sectional view of the syringe in its pre-injection condition illustrating an inserted release tab.

FIG. 5 is an enlarged, fragmentary cross-sectional view of the syringe shown in FIG. 1 illustrating the protective sheath in the expanded state covering the distal end of the needle.

FIG. 6 is an enlarged, fragmentary cross-sectional view of the present invention hypodermic syringe illustrating an alternative embodiment of the release tab.

FIG. 7 is an enlarged, partial cross-sectional view of the present invention hypodermic syringe utilizing a needle hub adapted to be coupled to a vacuum evacuation tube.

FIG. 8 is a partial, cross-sectional view of the present invention hypodermic syringe illustrating an alternative embodiment of the protective sheath.

DESCRIPTION OF THE PRESENTLY PREFERRED EMBODIMENT

An understanding of the present invention triple chambered syringe can be best understood from FIG. 1 wherein a side elevation, cross-sectional view is shown, the syringe generally being designated by the reference numeral 10. Syringe employs a central chamber 11 and a pair of slide chambers 12 and 13. Slide chambers 12 and 13 are positioned in diametric opposition to the axis of central chamber 11 and are in a parallel, equally spaced, relationship thereto. Central chamber 11 is used to store fluid medication or, in an alternative embodiment described hereinbelow, it can be employed to communicate with a conventional vacuum blood evacuation tube. As can be seen in FIG. 1 and FIG. 2, chambers 11, 12 and 13 are cylindrical in profile and extend the full length of syringe 10. The upper axial terminus of slide chambers 12 and 13 are enclosed by upper walls 14 and 15, respectively, the lower axial terminus of chambers 12 and 13 being open. Although the preferred embodiment employs two slide chambers 12 and 13, it is understood the objectives of the present invention could be implemented using more than two slide chambers, all of which are symmetrically disposed about central chamber 11.

Hypodermic needle 16 is secured within needle hub 17, the latter being coupled through wall 18 and being coaxially aligned with central chamber 11. Needle hub 17 permits needle 16 to communicate directly with the interior of central chamber 11. The embodiment of the present invention syringe 10 shown in FIG. 1 employs a conventional slider 19 which is used when injecting medication into a patient. In the alternative embodiment shown in FIG. 7, needle 16 is secured within a needle hub 20 which includes an extension 21 which can be coupled to conventional vacuum blood evacuation tubes.

FIG. 1 illustrates the present invention employing a protective sheath 25 in a state which exposes the distal end 26 of needle 16 prior to use of syringe 10. In the form of the present invention shown in FIG. 1 and FIG. 3, protective sheath 25 comprises a cylindrical member 27, the upper end thereof being open and adapted to be concentrically disposed about needle hub 17. The lower terminus of cylindrical member 27 extends inwardly into a series of radially biased flaps 28, each being separated from an adjacent flap along the radius of cylindrical members 27 of protective sheath 25. The center of the adjacent flaps is adapted to slidably move along the surface of needle 16. As shown in FIG. 1, prior to use, flaps 28 are biased in a manner which will allow protective sheath 25 to move downwardly along the surface of needle 16 toward the distal end 26 of needle 16.

Sheath guides 30 and 31 are cylindrical in profile and are adapted to be coaxially slidable within slide chambers 12 and 13, respectively. The upper ends of slide guides 30 and 31 are enclosed at walls 32 and 33 respectively. A helical spring 34 is disposed within slide chamber 12 and is placed intermediate upper wall 14 of slide chamber 12 and upper wall 32 of slide guide 30. In a like manner, helical spring 35 is disposed within slide chamber 13 intermediate upper wall 15 of slide chamber 13 and wall 33 of slide guide 31.

Protective sheath 25 is coupled to slide guides 30 and 31 at lower walls 40 and 41, respectively. Sheath arms 42 and 43 are laterally secured to cylindrical member 27 of protective sheath 25. Sheath arms 42 and 43 are identical in length and separation to insure that protective sheath 25 can be uniformly urged upwardly or downwardly along the surface of needle 16. Sheath arm 42 is conventionally coupled to lower wall 40 of sheath guide 30. In a like manner, sheath arm 43 is coupled to lower wall 41 of sheath guide 31.

FIG. 1 illustrates the present invention in the preinjection condition whereby the distal end 26 of needle 16 is exposed through protective sheath 25. To maintain the preinjection condition for syringe 10, helical springs 34 and 35 are compressed through the upward movement of sheath guides 30 and 31, respectively. Release tab 50 is used to maintain the preinjection position of protective sheath 25. As shown in FIG. 4, an aperture 51 is disposed through the outer wall of slide chamber 13, aperture 51 being adapted to be aligned with aperture 52 which is disposed through sheath guide 31, apertures 51 and 52 being adapted to be aligned with one another when sheath guide 31 is moved upwardly toward upper wall 15 thereby compression helical spring 35 between walls 15 and 33. Although FIG. 4 illustrates only the structure relating to sheath guide 31 and slide chamber 33, it is understood the positioning of apertures through the walls of sheath guide 30 and slide chamber 12 is identical.

As can be seen in FIGS. 1, 3 and 4, release tab 50 comprises a pair of latching pins 60 and 61 secured to each other by an integral band 62. When tabs 60 and 61 are in place, sheath guides 30 and 31 are maintained in position to compress helical springs 34 and 35. Since both tabs 60 and 61 must be removed to permit uniform movement of protective sheath toward the distal end 26 of needle 16, both can be withdrawn by applying an outwardly directed force on band 62.

FIG. 6 illustrates an alternative embodiment for implementing release tabs 50. FIG. 6 illustrates the release mechanism employed intermediate sheath guide 31 and slide chamber 13. It is understood the release mechanism used with respect to slide guide 30 and slide chamber 12 is identical. As with the structures shown in FIG. 4, aligned apertures 51 and 52 are disposed through the wall of slide chamber 13 and sheath guide 31, respectively. A biased catch 65 is adapted to maintain sheath guide 31 in place and comprising helical spring 35 prior to activation. Catch 65 consists of a biased flange 66 which is secured at one end thereof to the interior wall of sheath guide 31, the other end having extending therefrom a projection 67 which extends into apertures 51 and 52 and maintains the relative alignment between sheath guide 31 and slide chamber 13 prior to use of syringe 10. The protective sheath 25 is activated when latch 65 is depressed inwardly withdrawing projection 67 from apertures 51 and 52. Activation tab 68 consists of biased flange 69 which is secured at one end thereof to the exterior wall of syringe 10, the other end having projection pin 70 which extends into aperture 51. By depressing flange 69 inwardly toward central chamber 11, projection 70 will cause projection pin 67 to be internally withdrawn from aperture 51 thereby allowing helical spring 35 to move to its extended position urging sheath guide 31 toward the distal end 26 of needle 16. Therefore, the concurrent depression of the release tabs shown in FIG. 6 will result in the concurrent movement of sheath guides 30 and 31 relative to slide chambers 12 and 13, respectively.

The operation of the present invention can be best understood by reference to FIG. 5. Irrespective of whether the release tab 50 employs the structure shown in FIG. 4 or FIG. 6, activation of sheath guide 25 is accomplished when sheath guides 12 and 13 are caused to concurrently move toward the distal end 26 of needle 16. In FIG. 5, helical springs 34 and 35 are fully extended, the concurrent movement of sheath guides 12 and 13 resulting in movement of the sheath arm 42 and 43 in the directions shown. Since flaps 28 are biased to permit protective sheath 25 to easily move toward the distal end 26 of needle 16, once protective sheath 25 is extended beyond distal end 26, flaps 28 will close the aperture previously occupied by the needle thereby enclosing distal end 26 of needle 16 within the protective structure of sheath 25.

FIG. 8 illustrates an alternative embodiment of protective sheath 73 which is intended to insure that distal end 26 of needle 16 cannot inadvertently be urged through the aperture 74 formed in the base 75 of protective sheath 73. In the embodiment shown in FIG. 8, the length of sheath arm 76 is greater than the length of sheath arm 77 and is therefore biased relative to sheath arm 77 creating a clockwise force. In its pre-injection state, the bias created by the configuration of sheath arms 76 and 77 will cause no misalignment since the needle 16 will centrally penetrate aperture 74 in the same manner shown in FIG. 3. When the releasing tabs activate sheath guides 12 and 13, and the protective sheath 73 travels beyond distal end 26 of needle 16, the biased force caused by the misalignment of sheath arms 76 and 77 will off-set protective sheath 73 relative to distal end 26. Distal end 26 will be misaligned relative to the axis of protective sheath 73 (i.e., aperture 74) thereby preventing later inadvertent contact with the distal end 26 of needle 16. In the embodiment shown in FIG. 8, slide chambers 30 and 31 are in a diametrically opposed relationship to central chamber 11. It is understood that the misalignment of the protective sheath 73 can also be accomplished with sheath arms of equal length and the displacement of the slide chambers so that they are not in diametric opposition relative to central chamber 11.

A second embodiment of the present invention can be best understood by reference to FIG. 8. In the embodiment shown in FIG. 8, the length of sheath arm 76 is greater than the length of sheath arm 77. The purpose of employing sheath arms having different lengths is to create a biasing force which will offset protective sheath 73 with respect to distal end 26 of needle 16. The misalignment of protective sheath 73 with respect to the distal end 26 of needle 16 can be accomplished in an alternative manner. The alternative embodiment employs a coupling between a single slide chamber and protective sheath 73. The structure of the alternative embodiment includes only a unitary coupling between slide chamber 31 and protective sheath 73. In such an embodiment, sheath arm 76 is displaced from the longitudinal axis of slide chamber 31 and is oriented toward needle 16. Prior to activation, needle 16 will extend through aperture 74 of protective sheath 73, the orientation of sheath arm 76 relative to the axis of slide chamber 31 causing base 75 to exert a lateral force against the shank of needle 16. When activation causes protective sheath 73 to be extended beyond the distal end 26, the misalignment of sheath arm 76 relative to the axis of slide chamber 31 causes misalignment between aperture 74 and the distal end 26 of needle 16. By off-setting aperture 74 relative to the distal end 26 of needle 16, distal end 26 of needle 16 will be shielded from inadvertent contact.

It can therefore be seen the primary objectives of the present invention are achieved through the use of the triple chambered syringe. Prior to and during use of the syringe, one has a clear and unobstructed view of the entry point. Most importantly, the distal end 26 of needle 16 can be enclosed within protective sheath 25 either during use or after removal of needle tip 26 by activation of release tab 50 which causes helical springs 34 and 35 to extend thereby urging protective sheath 25 axially beyond the distal end 26 of needle 16.

I claim:

1. A hypodermic syringe including a protective sheath for enclosing the distal end of a needle comprising:
   (a) a syringe body having a cylindrical central chamber and at least one slide chamber disposed adjacent said central chamber and being in parallel spaced relation therewith;
   (b) an injection needle including a chamber hub, a shank and a distal end, the chamber hub being coupled to the central chamber, said shank and distal end being axially aligned with and extending from said central chamber;
   (c) a protective sheath including a cylindrical member having an open upper end and a plurality of biased flaps radially depending inwardly from the lower end of said cylindrical member and being adapted to be concentrically disposed about the shank of said injection needle;
   (d) biasing means disposed within said slide chamber for providing a force to urge said protective sheath toward the distal end of said injection needle;
   (e) means for coupling said biasing means to said protective sheath; and
   (f) release means for limiting the movement of said protective sheath toward the distal end of said injection needle coupled intermediate said biasing means and said syringe body.

2. A hypodermic syringe as defined in claim 1 wherein the syringe body has a cylindrical central chamber and two slide chambers which are diametrically disposed on opposed sides of said central chamber.

3. A hypodermic syringe as defined in claim 2 wherein said chamber hub includes means for communicating with a vacuum blood evacuation tube.

4. A hypodermic syringe as defined in claim 2 wherein said biasing means comprises a pair of cylindrical sheath guides having upper and lower walls, each being slidably disposed within one of said slide chambers and a helical spring disposed within said slide chambers adjacent the upper wall of each of said sheath guides.

5. A hypodermic syringe as defined in claim 4 wherein said release means comprises detachable release tabs removeably disposed through each of said slide chambers and being coupled to said cylindrical sheath guides whereby said helical springs are maintained in a compressed state.

6. A hypodermic syringe as defined in claim 4 wherein said release means comprises a biased member secured to the inner cylindrical wall of each of said sheath guides, a projection extending radially outwardly therefrom and movably disposed through aligned apertures formed in each of said cylindrical sheath guides and syringe body, and activation means for depressing each of said projections coupled to the syringe body.

7. A hypodermic syringe as defined in claim 4 wherein said means for coupling said biasing means to said protective sheath comprises a pair of extension arms, one end of each being coupled to the lower wall of a respective one of said cylindrical sheath guides, the second end of each of said extension arms being secured to the cylindrical wall of said protective sheath in diametric opposition to one another.

8. A hypodermic syringe as defined in claim 7 wherein said extension arms are of equal length.

9. A hypodermic syringe as defined in claim 7 wherein the length of one of said extension arms is greater than that of the other whereby said protective sheath is misaligned when said protective sheath is urged toward the distal end of said injection needle.

10. A hypodermic syringe as defined in claim 1 wherein said biasing means comprises a cylindrical sheath guide having upper and lower walls and being slidably disposed within said slide chamber and a helical spring disposed within the slide chamber adjacent the upper wall of said sheath guide, said means for coupling said biasing means to said protective sheath comprising an extension arm, one end being coupled to the lower wall of said cylindrical sheath guide, the second end of said extension arm being secured to the cylindrical wall of said protective sheath, said extension arm laterally biasing said protective sheath relative to the injection needle.

11. A hypodermic syringe including a protective sheath for enclosing the distal end of a needle comprising:
(a) a syringe body having a cylindrical central member and a pair of cylindrical slide chambers, each of said slide chambers being parallel to and equally spaced from said central chamber on opposite sides thereof, the upper ends of each of said slide chambers being enclosed;
(b) an injection needle including a chamber hub, a shank and a distal end, the chamber hub being coupled to the central chamber, said shank and distal end being axially aligned with an extending from said central chamber;
(c) a pair of cylindrical sheath guides each being slidably disposed within one of said slide chambers, the upper end of each of said cylindrical sheath guides being enclosed;
(d) a helical spring disposed within each of said slide chambers intermediate the enclosed upper end thereof and the enclosed upper end of said sheath guides;
(e) a protective sheath comprising a cylindrical member having an open upper end and a plurality of biased flaps integral with and radially depending inwardly from the lower end of said cylindrical member and being adapted to be concentrically disposed about the shank of said injection needle whereby the protective sheath can be slidably moved along the shank of the injection needle from the vicinity of the chamber hub to beyond the distal end of the injection needle;
(f) a pair of sheath arms, each having integral first and second members, each of the first members being secured to the lower end of one of said sheath guides and being coaxial therewith, the second members being coupled to the cylindrical member of said protective sheath; and
(g) release means for maintaining the predetermined relationship between the sheath guides and the syringe body and providing means for said protective sheath to move toward the distal end of said injection needle, said release means being removeably coupled to said sheath guides and syringe body.

12. A hypodermic syringe as defined in claim 10 wherein said chamber hub includes means for communicating with a vacuum blood evacuation tube.

13. A hypodermic syringe as defined in claim 10 wherein said release means comprises detachable release tabs removeably disposed through each of said slide chambers and being coupled to said cylindrical sheath guides whereby said helical springs are maintained in a compressed state.

14. A hypodermic syringe as defined in claim 10 wherein said release means comprises a biased member secured to the inner cylindrical wall of each of said sheath guides, a projection extending radially outwardly therefrom and movably disposed through aligned apertures formed in each of said cylindrical sheath guides and syringe body, and activation means for depressing each of said projections coupled to the syringe body.

15. A hypodermic syringe as defined in claim 10 wherein the first members of said sheath arms are of different lengths whereby said protective sheath is misaligned when said protective sheath is urged beyond the distal end of said injection needle.

* * * * *